(12) United States Patent
Rossi et al.

(10) Patent No.: US 9,470,222 B2
(45) Date of Patent: Oct. 18, 2016

(54) PERISTALTIC PUMP AND AN ADJUSTMENT MECHANISM

(75) Inventors: Markus Rossi, Joutseno (FI); Anssi Tujula, Vainikkala (FI)

(73) Assignee: FLOWROX OY, Lappeenranta (FI)

( * ) Notice: Subject to any disclaimer, the term of this patent is extended or adjusted under 35 U.S.C. 154(b) by 197 days.

(21) Appl. No.: 14/344,807

(22) PCT Filed: Oct. 14, 2011

(86) PCT No.: PCT/FI2011/050894
§ 371 (c)(1),
(2), (4) Date: Mar. 13, 2014

(87) PCT Pub. No.: WO2013/053982
PCT Pub. Date: Apr. 18, 2013

(65) Prior Publication Data
US 2014/0341765 A1 Nov. 20, 2014

(51) Int. Cl.
*F04B 43/08* (2006.01)
*F04B 43/12* (2006.01)
*A61M 5/142* (2006.01)

(52) U.S. Cl.
CPC ........... *F04B 43/1276* (2013.01); *F04B 43/08* (2013.01); *F04B 43/1261* (2013.01); *F04B 43/1284* (2013.01); *A61M 5/14232* (2013.01)

(58) Field of Classification Search
CPC .. F04B 43/12; F04B 43/123; F04B 43/1238; F04B 43/1253; F04B 43/1276; F04B 43/1284; F04B 45/08; A61M 5/142
See application file for complete search history.

(56) References Cited

U.S. PATENT DOCUMENTS 7,726,956 B2 6/2010 Riihimäki
2010/0129247 A1 5/2010 Lauer

OTHER PUBLICATIONS

Jul. 5, 2012 International Search Report issued in International Patent Application No. PCT/FI2011/050894.
Jul. 5, 2012 Written Opinion issued in International Patent Application No. PCT/FI2011/050894.

*Primary Examiner* — Patrick Hamo
(74) *Attorney, Agent, or Firm* — Oliff PLC

(57) ABSTRACT

This invention concerns peristaltic pumps and an adjustment mechanism for adjusting a compression force imposed on a hose. The adjustment mechanism includes at least a gear unit and a counterpart for the gear unit. The counterpart is operatively coupled to a rotor, wherein the gear unit in cooperation with the counterpart are configured to adjust a gap between the rotor outer surface and the pump cavity inner perimeter.

9 Claims, 8 Drawing Sheets

D-D

PERISTALTIC PUMP AND AN ADJUSTMENT MECHANISM

CROSS-REFERENCE TO RELATED APPLICATIONS

This application is a National Phase of an international application PCT/FI2011/050894 filed Oct. 14, 2011.

FIELD OF THE INVENTION

This invention relates generally to peristaltic pumps and particularly to an adjustment mechanism for the peristaltic pump for adjusting the compression force imposed on a hose/tube.

BACKGROUND OF THE INVENTION

Positive displacement pumps, in which peristaltic pumps form a subclass, are employed for pumping problematic substances in particular, such as abrasive, corrosive, slurried or high-viscosity liquids and liquid-suspended solids. Peristaltic pumps are also preferred when pumping as a primary function must be complemented with accurate metering, high hygienic standard and leakproofness. Peristaltic pumps are used widely e.g. in the manufacture of foodstuffs, drugs, oil and chemical products. In heavy industries, peristaltic pumps serve to pump, inter alia, such materials as liquids and ore/mineral suspensions.

To operate properly, a peristaltic pump must be capable of forcing a volume of a fluid medium to move along a hose/tube by way of peristaltically compressing the hose from end to end during one turn of the pump rotor while simultaneously the next fluid volume is already filling the hose. Conventionally, this pumping sequence is implemented by rotating a nonrotary shoe or pressing roller, whereby the hose is subjected to progressive compression in the nip between the shoe/roller and the peripheral wall of the pump head. Furthermore, the hose/tube/tubing is selected to be sufficiently elastic and reinforces such that the hose resumes its circular profile immediately after the compression thereby creating a vacuum in its lumen thus including the entry of the next volume of the fluid medium into the hose.

Prior a publication U.S. Pat. No. 7,726,956, the solutions of related art lacked an adjustment mechanism for setting the compressive force in peristaltic pumps. More specifically, no facility was provided for setting the compression applied on the pump hose or like elastic flow channel, whereby the distance between the rotor and the pump cavity couldn't be varied from a constant value.

However, the publication U.S. Pat. No. 7,726,956 was targeted to such a need and it discloses a peristaltic pump that comprises an adjustment mechanism. A peristaltic pump according to the publication is shown in FIG. 1. The pump comprises a pump body 1, a hose 2 and a rotor 3. The rotor 3 is mounted freely rotatable on bearings mounted onto an eccentric adjustment bushing 5. In use, the rotor 3 rotates in the pump cavity and compresses the hose 2 in said pump cavity by rolling over the hose surface thus propelling the bulk of fluid medium contained in the hose 2. With the rotary progressive motion of the rotor 3 and the hose recovering its circular profile immediately after the point of rotor compression, the hose 2 creates a vacuum that causes the hose 2 to become refilled with the fluid medium being pumped. The adjustment mechanism serves to adjust the gap between the rotor outer surface and the pump cavity inner periphery that determines the compressive force imposed on the hose. The eccentric adjustment assembly disclosed in U.S. Pat. No. 7,726,956 allows runtime adjustment of hose compression to be carried out with a calibrated torque wrench. A worm gear is shaped to be rotatable by means of the torque wrench. As the worm is thus turned with the torque wrench, an accurately set torque can be applied during rotation of the worm. With the applied torque thus being always constant, also the compressive force imposed on the hose becomes sufficiently accurately set to an constant value.

SUMMARY OF THE INVENTION

The present invention is targeted to peristaltic pumps where compression force can be set more easily compared to the solutions of related art.

The present application discloses a peristaltic pump and an adjustment mechanism for setting the compression force applied on the pump hose.

According to a first aspect, there is provided a peristaltic pump comprising at least an assembly comprising at least a rotor configured to compress a hose/tube being positioned on a pump cavity inner perimeter and an adjustment mechanism configured to adjust the compression force imposed on the hose/tube, said assembly being coupled to a crankshaft of the pump body, wherein the adjustment mechanism comprises at least of a gear unit and a counterpart for said gear unit, said counterpart being operatively coupled to said rotor, wherein the gear unit in cooperation with the counterpart are configured to adjust a gap between the rotor outer surface and the pump cavity inner perimeter.

According to a second aspect, there is provided an apparatus for a peristaltic pump, said apparatus comprising a rotor configured to compress a hose/tube being positioned on a pump cavity inner perimeter, and an adjustment mechanism configured to adjust the compression force imposed on the hose/tube, said apparatus suitable for being coupled to a crankshaft of the pump body, wherein the adjustment mechanism comprises at least a gear unit and a counterpart for the gear unit, said counterpart being operatively coupled to said rotor, wherein the gear unit in cooperation with the counterpart are configured to adjust a gap between the rotor outer surface and the pump cavity inner perimeter.

According to an embodiment, supporting means are provided to support said hose/tube.

According to another embodiment, the peristaltic pump comprises bearings of the crankshaft being arranged within the pump cavity.

According to another embodiment, locking means are provided to function in a locking position and a rest position, where the locking means in the locking position are configured to lock the adjustment mechanism, and wherein the locking means in the rest position are configured to enable the adjusting operation of the adjusting mechanism.

According to another embodiment, the gear unit is rotatable with a crank.

According to another embodiment the gear unit comprises a shaft and at least one gear on each end of the shaft.

According to another embodiment the counterpart for the gear unit comprises at least one counterpart piece on each end of the rotor.

The present solution enables manufacturing of peristaltic pumps with lower costs than pumps of related art. In addition, the present solution enables larger pumps that are capable of continuous, non-stop, performance.

DESCRIPTION OF THE DRAWINGS

In the following, various embodiments of the invention will be described in more detail with reference to the appended drawings, where.

DETAILED DESCRIPTION OF THE INVENTION

Figure 1:
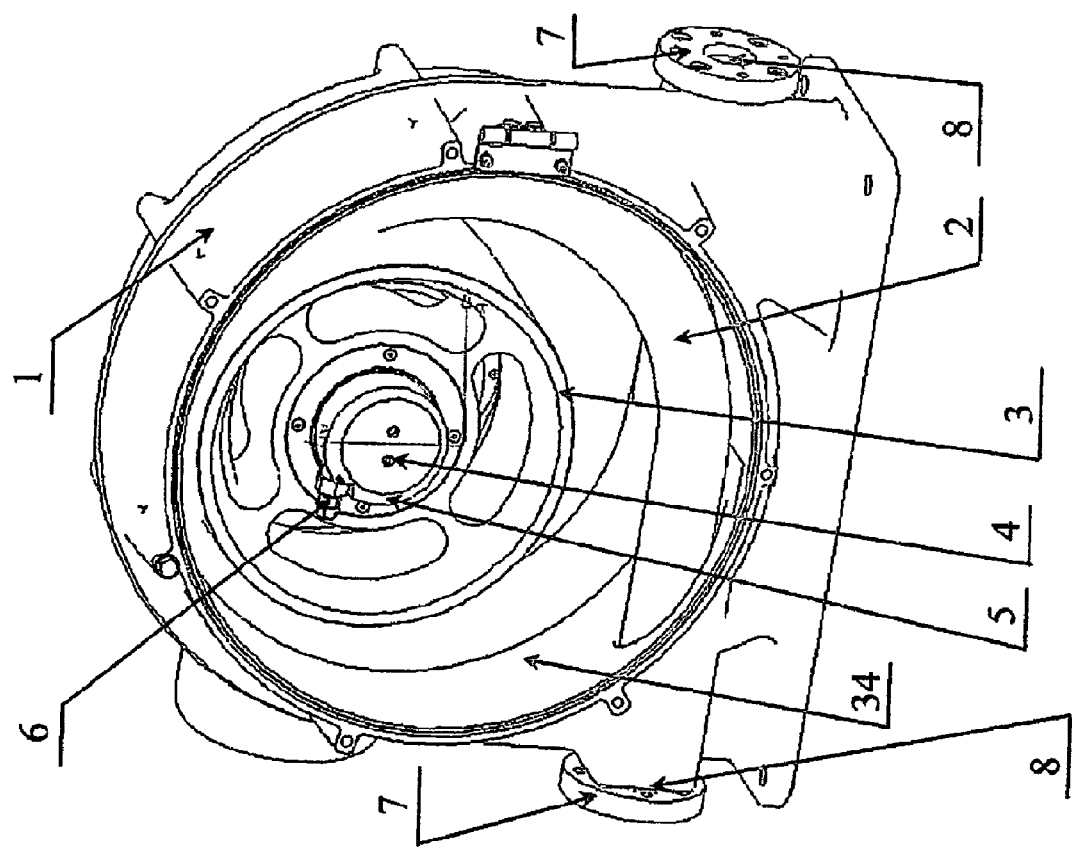
FIG. 1 illustrates a peristaltic hose pump according to prior art.
Figure 2:
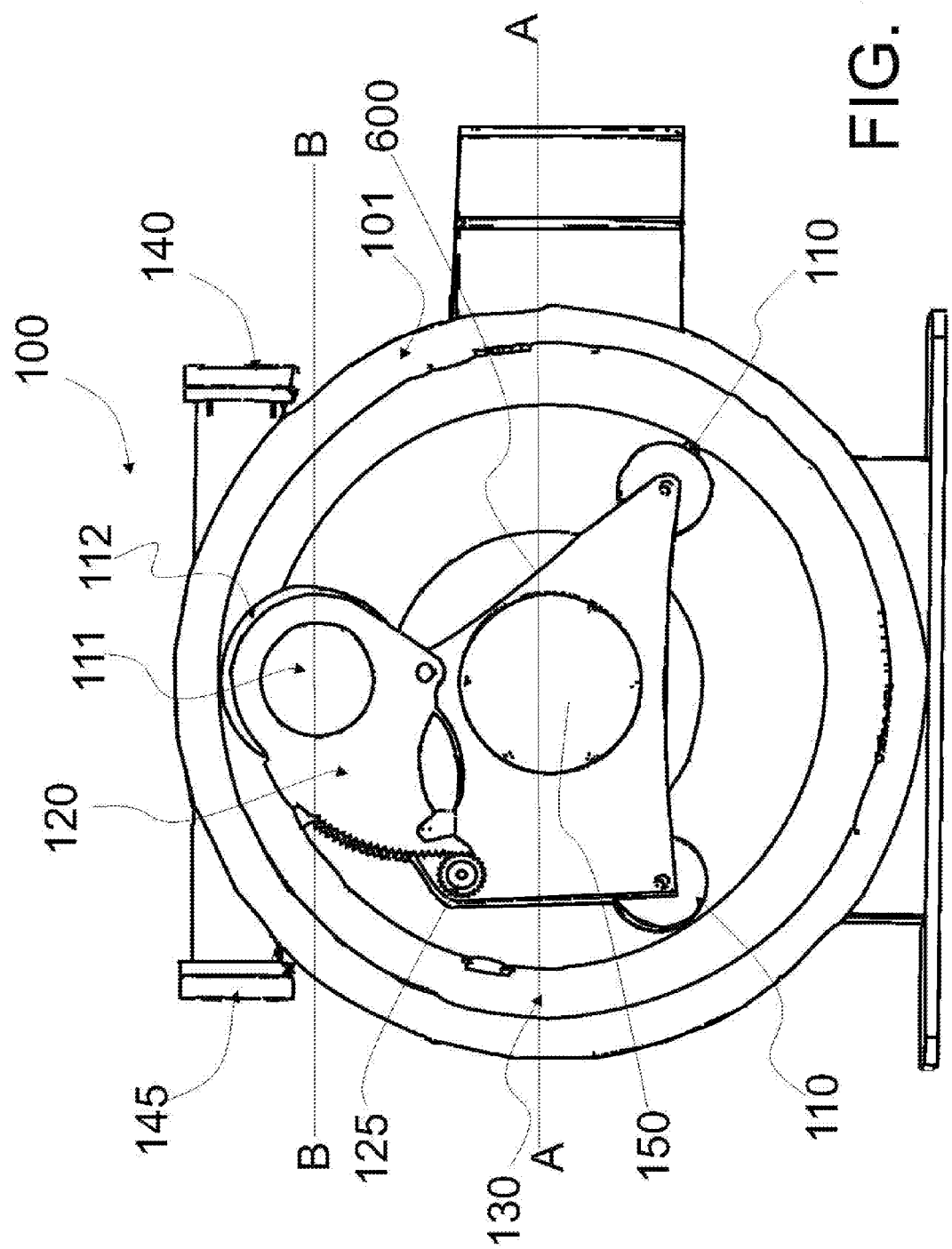
FIG. 2 illustrates an embodiment of a peristaltic hose pump comprising an adjustment mechanism according to an example of the present invention.

FIG. 2 illustrates an embodiment of a peristaltic hose pump comprising an adjustment mechanism. As in the pump of FIG. 1, the pump 100 shown in FIG. 2 also comprises a pump body 101, a hose 130, a rotor 112 and feedthrough openings 140, 145 for the hose 130. The hose 130 or like elastic pump tube or pump channel is inserted into the pump cavity with a sleigh 600 housed therein, whereby the hose rests against the pump cavity inner perimeter so as to cover a full circle. The hose ends can be captively fitted in feedthrough openings 140, 145 of the pump body. As a difference to the pump of FIG. 1, the pump of FIG. 2 comprises a sleigh 600 comprising an adjustment mechanism for setting the compression applied on the pump hose 130. The rotor 112, the end on which is shown with reference 111, is mounted freely rotatable manner on a bearings mounted onto the sleigh 600, and the rotor is configured to function as a pressing roller of the peristaltic pump.

An adjustment mechanism, being disclosed next, serves to adjust the gap between the rotor outer surface and the pump cavity inner periphery that determines the compressive force imposed on the hose. The adjustment mechanism is formed at least of a gear unit 125 and a corresponding counterpart 120. The gear unit 125 may comprise at least one gear, but in this example the gear unit 125 comprises two gears. The gear unit 125 is configured to operate with the counterpart 120, which counterpart 120 can be fixed to a shaft of the rotor 112.

The sleigh 600 is mounted on a crankshaft pin, one end of which is shown with reference numeral 150. The crankshaft is mounted freely rotatable on bearings on the rear wall of the pump body 101, centrally in regard to the pump cavity.

In use, and actuated by the drive means, the crankshaft forces the sleigh 600 to rotate in the pump cavity affecting the rotor 112 to compress the hose 130 in said pump cavity at a given distance from the interior perimeter of the pump cavity. In addition, the rotor 112 is configured to roll on the hose surface thus propelling the bulk of substance contained in the hose 130. The distance from the interior perimeter of the pump cavity and the rotor 112 can be defined by the adjustment mechanism and is dependent on the compression being applied to the hose 130. Hereby, the rotor 112 compresses the hose 130 inserted in the pump cavity so that, with the rotation of the sleigh 600 and with the rolling movement of the rotor 112, the volume of fluid medium being pumped and contained in the hose 130 in front of the rotor 112 is prevented from leaking in the reverse direction past the point of the hose 130 compressed by the rotor 112. With the rotary progressive motion of the rotor and the hose 130 recovering its circular profile immediately after the point of rotor compression, the hose 130 creates a vacuum that causes the hose 130 to become refilled with the fluid medium being pumped.

FIG. 2 also shows supporting means in the form of supporting rotors (i.e. rollers) 110 being operatively connected to the respective shoulders of the sleigh. The purpose of the supporting means 110 is to support the hose 130 so that the hose 130 maintains it circular profile and not slacken. Sections A-A and B-B are illustrated in FIG. 2 for more detailed discussion.

Figure 3:
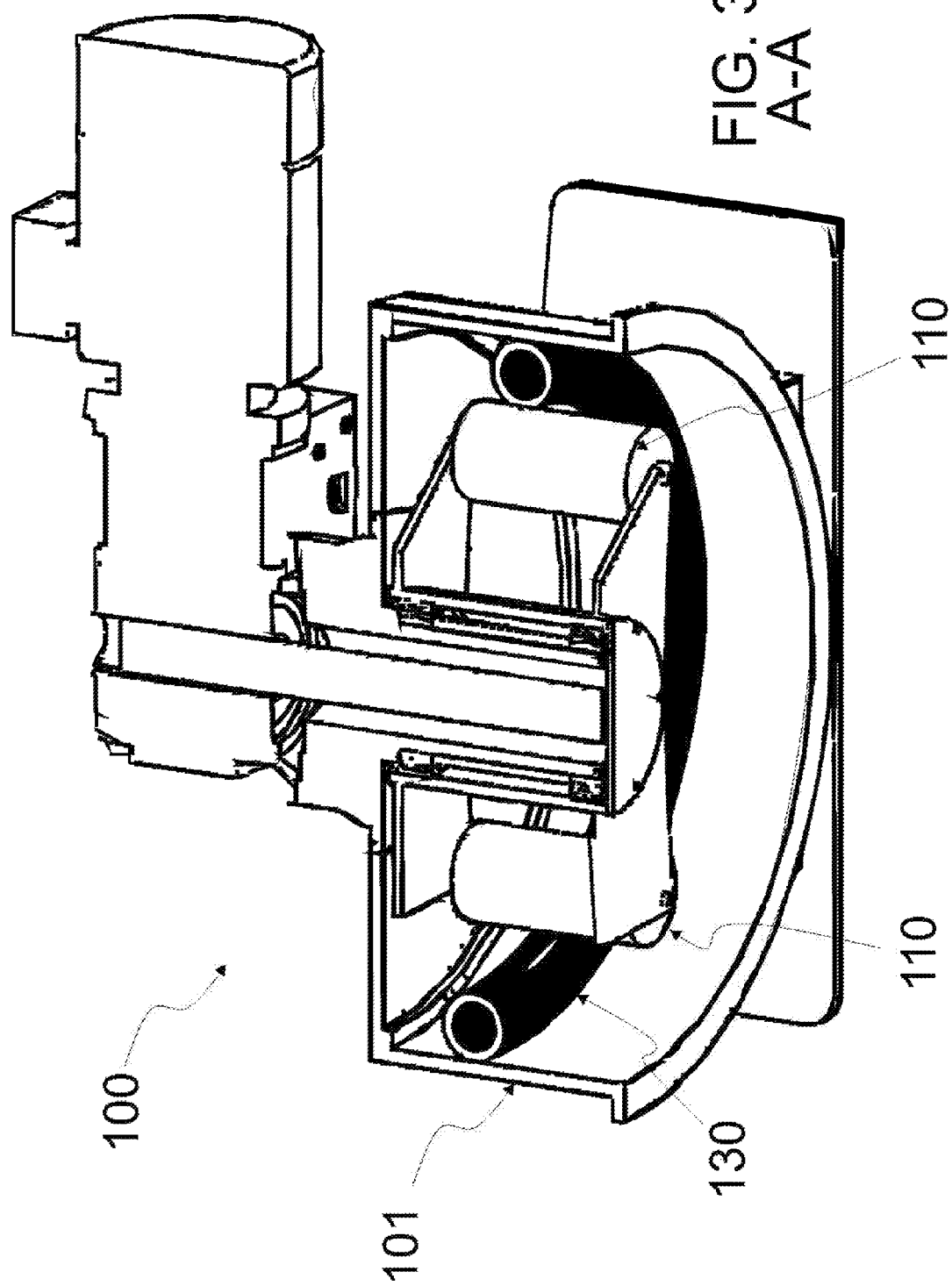
FIG. 3 illustrates a cross-sectional view of a section A-A of a peristaltic hose pump comprising supporting rollers.
Figure 4:
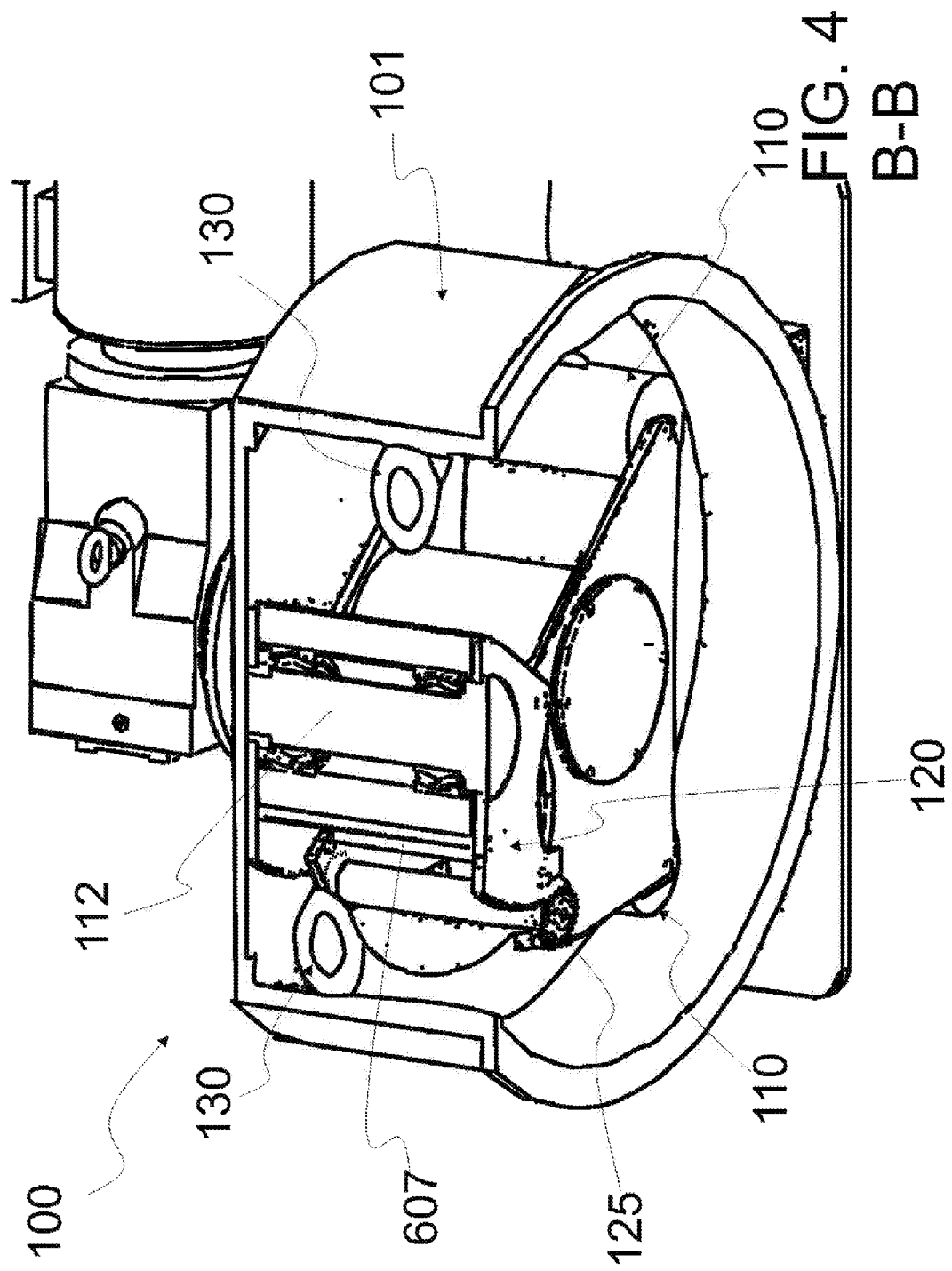
FIG. 4 illustrates a cross-sectional view of a section B-B of a peristaltic hose pump comprising an adjustment mechanism according to an example of the present invention.

FIG. 3 shows a view of the section A-A for the peristaltic hose pump 100 comprising supporting means 110 for supporting the hose 130 within the pump body 101. FIG. 4 shows a view of the section B-B for the peristaltic hose pump 100. From FIG. 4 it is possible to see the counterpart 120 for the gear unit 125, as well the rotor 112 being located between the pieces of counterpart 120. Also a locking bar 607, the purpose of which is discussed in more detailed manner in connection to FIG. 5, can be seen in FIG. 4. The hose 130 travels within the pump body 101 and can be supported by means the support means 110.

Figure 5:
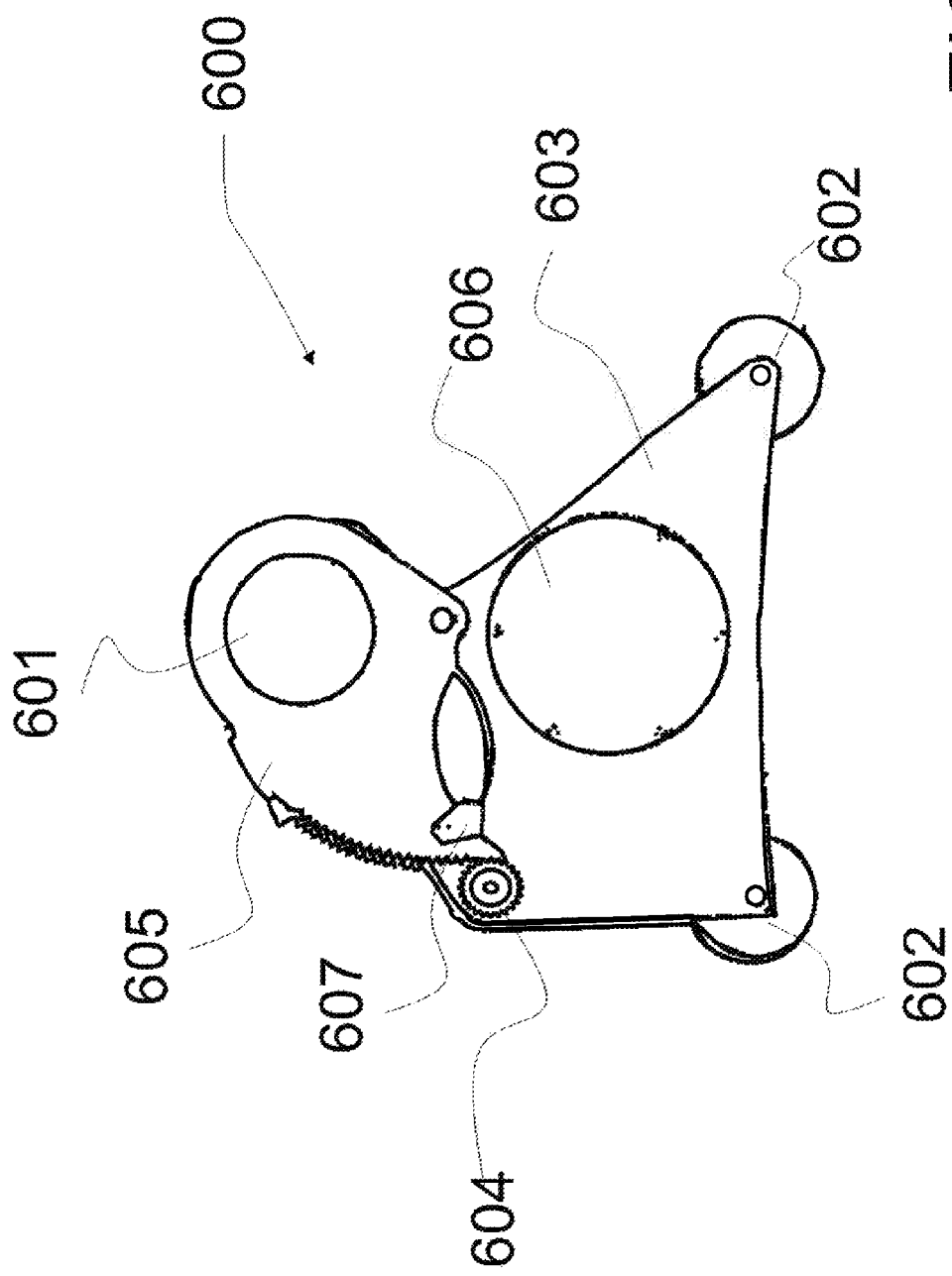
FIG. 5 illustrates an embodiment of the adjustment mechanism.

FIG. 5 illustrates the sleigh 600 according to an embodiment of the invention. In use, the sleigh 600 is placed in the cavity of the peristaltic pump. The sleigh comprises at least a rotor, the end 601 of which is shown in FIG. 5, a gear unit 604 and a counterpart 605 for the gear unit. As said, the gear unit 604 can be formed of two gears, at least one gear being located on each end of a shaft of the gear unit 604. The counterpart 605 can be formed corresponding counterpart pieces, between which the rotor can be installed. Therefore at least one counterpart piece (i.e. number corresponding the amount of gears in the gear unit) is located on each end of the rotor. In this example, there are one gear located on each end of the shaft of the gear unit, and one counterpart piece being located on each end of the rotor. However, the need for having more than one gears on each end of the shaft may raise with massive pumps, where e.g. two parallel gears on each end of the shaft are needed., The sleigh 600 can also comprise at least one support rotor 602 configured to support the hose during use. The support rotors 602 as well as the gear unit 604 and the counterpart 605 are coupled to a central unit 603 of the sleigh that is formed around a crankshaft the end 606 of which is shown in FIG. 5.

The counterpart 605 can be locked to the gear unit 604 by means of a locking means, such as a locking bar 607, for example, that is movable from a locking position (shown in FIG. 5) to a rest position. In the rest position of the locking bar 607, the gear unit's counterpart 605 is released from the operating position. By this, the gear unit 604 can be rotated, which—in turn—turns the counterpart 605 thus effecting to the rotor's location with respect to the inner wall of the peristaltic pump also. In this embodiment, the sleigh comprises one central unit 603, one gear unit 604, one counterpart 605 and one rotor (the end of which is shown with 601). However, other embodiments can comprise two gear units 604, two counterparts 605 and two rotors being coupled to one central unit 603. In addition, this embodiment shows two support rotors 602. However, other embodiments may have one or more than two, or none support rotors 602. Yet, an embodiment may have any amount N of support rotors (N=0, 1, 2, 3, . . . ) and in addition a support rotor configured around an shaft of the gear unit 604, or two support rotors configured around shafts of two gear units.

Figure 6:
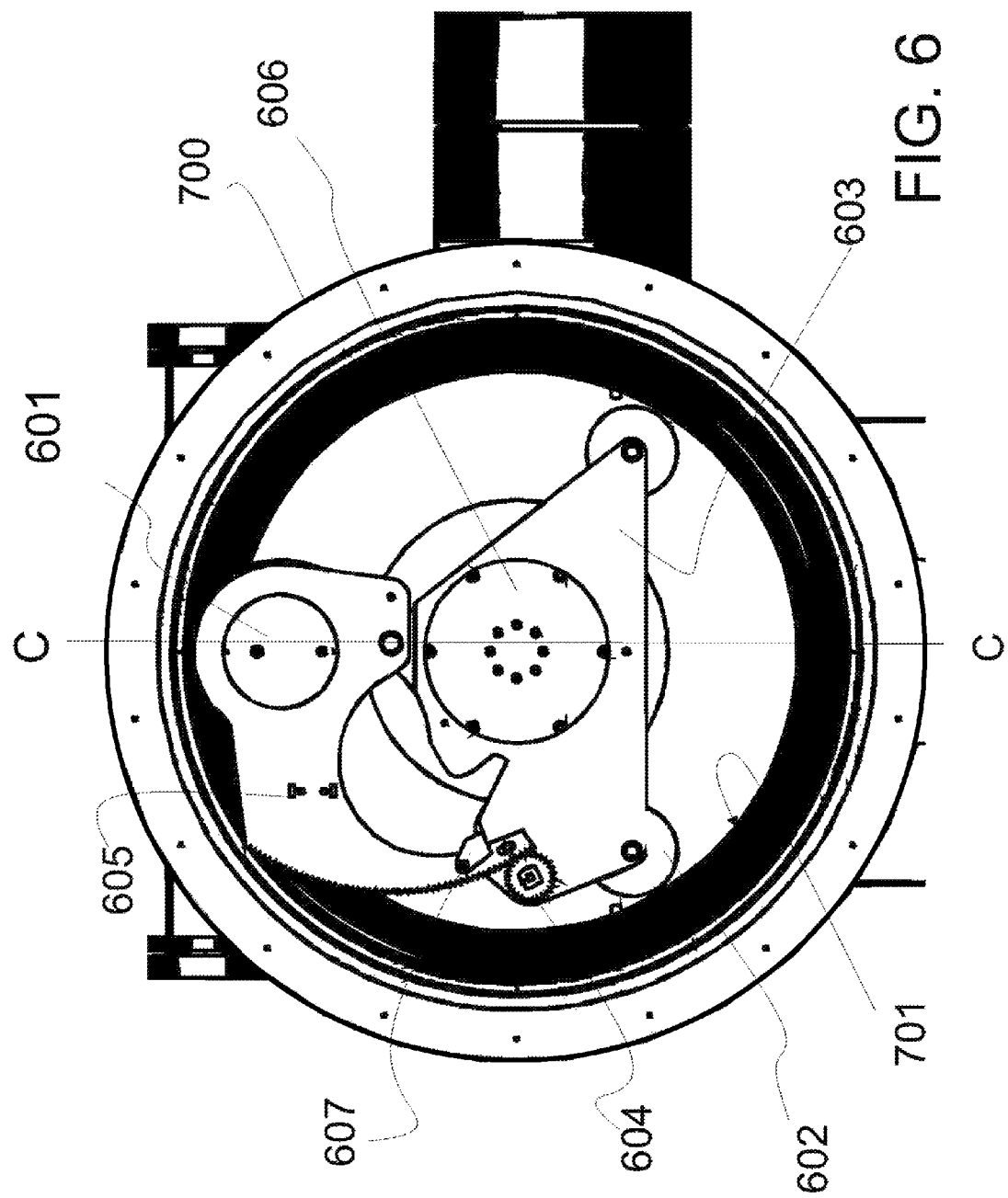
FIG. 6 illustrates a peristaltic pump having an adjustment mechanism according to an example of the present solution.

FIG. 6 illustrates an example of the sleigh 600 according to an embodiment of the invention. In this figure, the sleigh 600 is positioned within pump 700 cavity. The sleigh shown in this figure comprises the elements being shown in FIG. 5: a central unit 603, support rotors 602, a gear unit 604, a counterpart 605, a locking bar 607, an end 601 of a rotor and an end 606 of a crankshaft. In this FIG. 6, the locking bar 607 is in the locking position. Rotor's (the end of which is shown by 601) distance from the inner wall of the pump cavity is the smallest and the compression force applied to the hose 701 is the greatest. In order to enlarge the distance between the rotor (the end of which is shown by 601) and the inner wall of the pump cavity, the position of the locking bar 607 is moved to the rest position, whereby the counterpart 605 is released. By rotating the gear unit 604 (e.g. with help of a crank or similar), the counterpart 605 can be rotated towards the crankshaft. The counterpart 605 can be rotated as much as is needed for adjusting the distance between the rotor (end of which is referred with 601) and the inner wall of the pump cavity. The distance can be adjusted according to the pump's output pressure (e.g. 0-16 bar or different) for the substance within the hose. FIG. 6 also shows a section C-C for FIG. 7.

Figure 7:
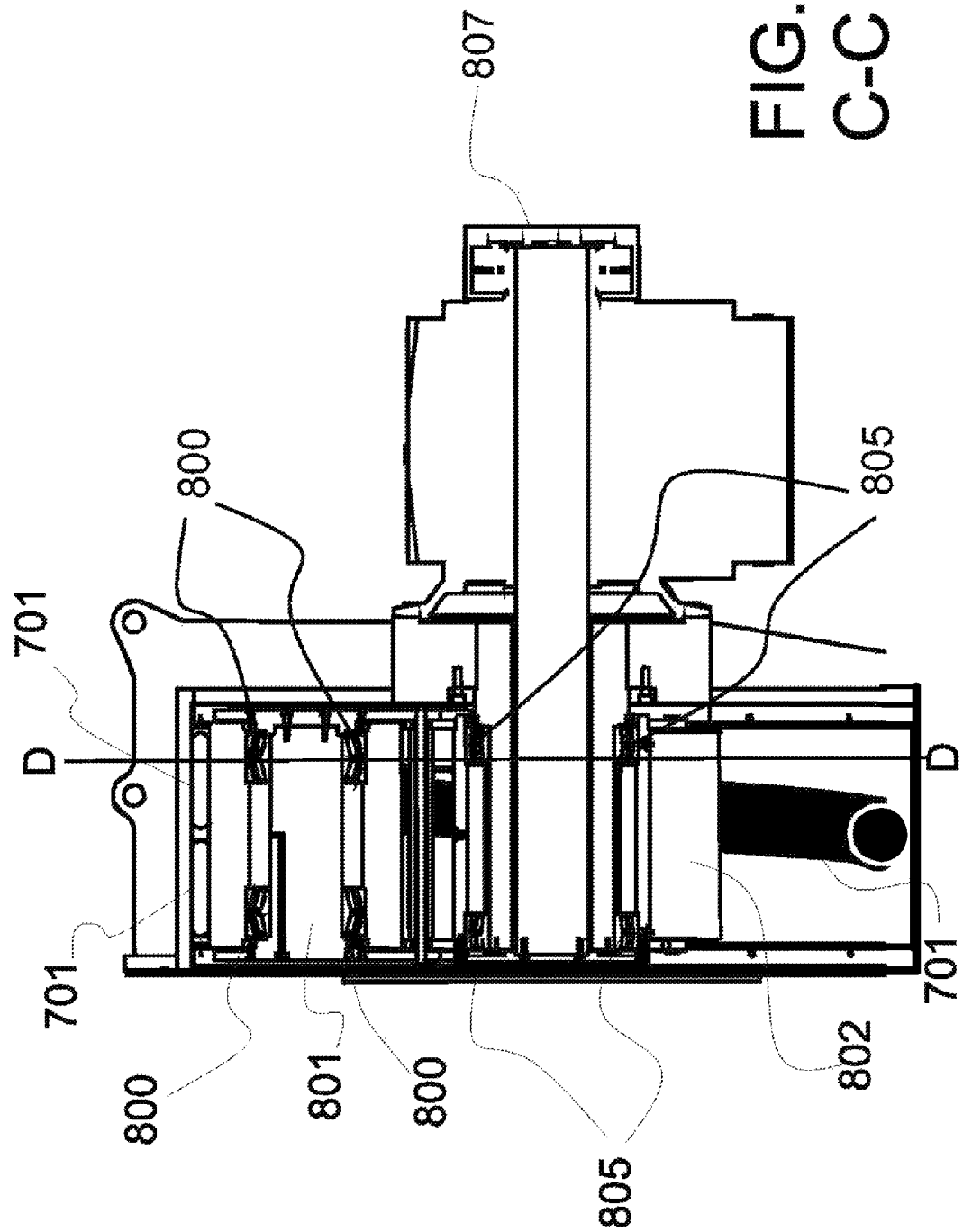
FIG. 7 illustrates a cross-sectional view of section C-C of the peristaltic pump comprising an adjustment mechanism according to an example of the present invention.

FIG. 7 is a cross-sectional view of the pump of FIG. 6 viewed from section C-C. The purpose of FIG. 7 is to show an embodiment of the bearings arrangement for the present invention. The bearings 800 of the rotor 801, and the bearings 805 of the pump body are positioned within the pump cavity, thus forming an internal bearings arrangement. This deviates from the pump of prior art, which has the bearings of the pump body outside the pump cavity. With the present arrangement, no bending moment is targeted to the bearings of the pump body, but the pump cavity is capable of carrying it all. FIG. 7 also shows one support rotor 802 and a crankshaft 807. Yet, FIG. 7 shows the hose 701. FIG. 7 also shows a section D-D for FIG. 8.

Figure 8:
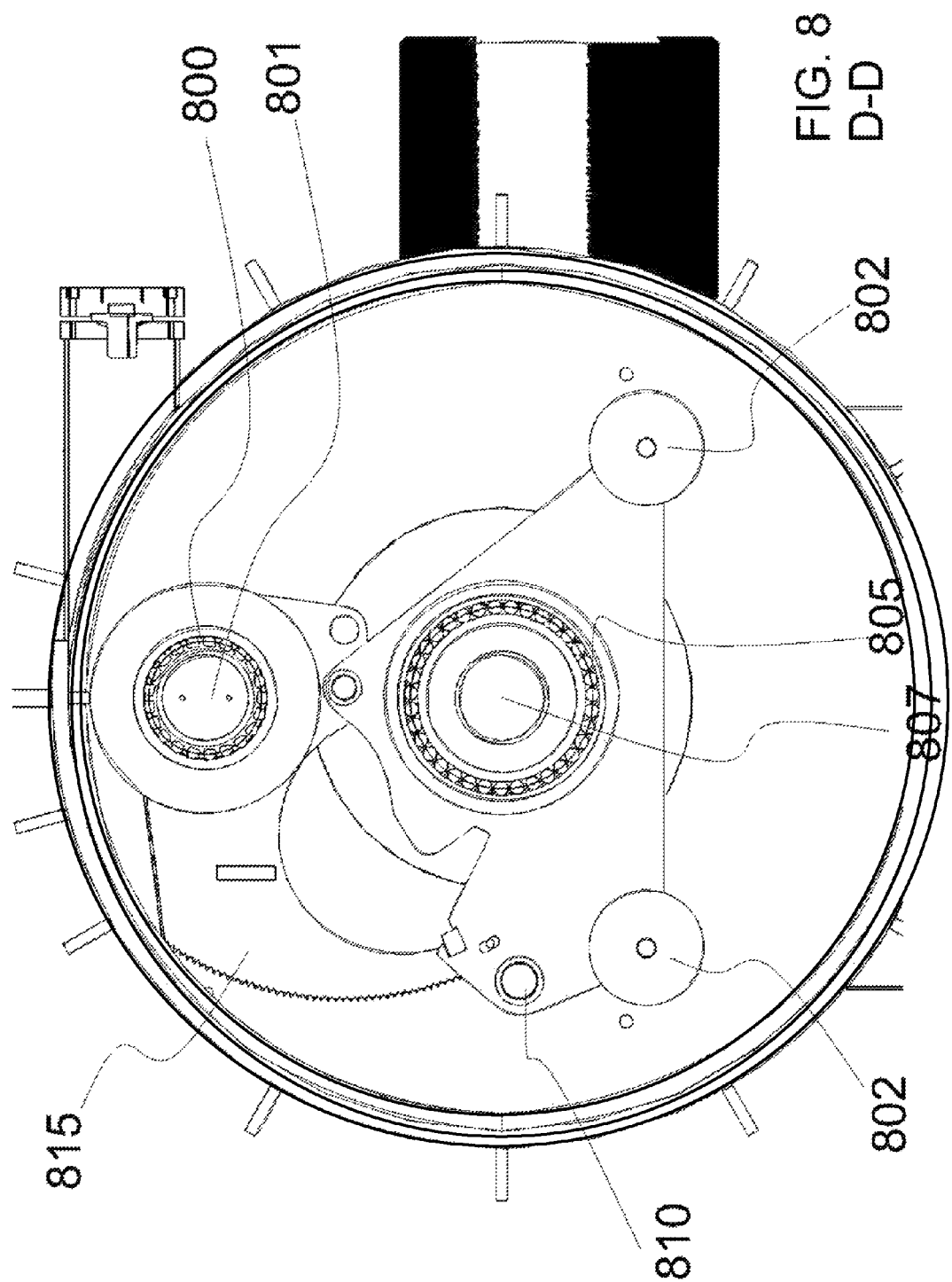
FIG. 8 illustrates a cross-sectional view of a section D-D of the peristaltic pump comprising an adjustment mechanism according to an example of the present invention.

FIG. 8 is a cross-sectional view of the pump of FIG. 6 viewed from section D-D of FIG. 7. The purpose of FIG. 8 is to show the internal bearings arrangement for the peristaltic pump, where both bearings 800 of the rotor 801 and the bearings 805 of the pump body are situated within the pump cavity. In addition to the bearings arrangement, FIG. 8 shows a shaft 810 of the gear unit, one piece 815 of the gear unit's counterpart. The support rotors 802 are also illustrated in FIG. 8.

In the previous, a mechanism for adjusting the compression force (distance between the pressing roller and the inner wall of the peristaltic pump) applied on the pump hose has been disclosed by means of examples. The main reason for the adjustment is that the compression force need to be varied according to the pumping pressure for the substance. Another reason for the adjustment can be found from a characteristic property of the peristaltic pump based on positive displacement, which is that the inner surface of the hose/tube erodes during pumping. This process reduces the hose wall thickness and, thence, the compression of the hose in the gap between the pump rotor and body. Hence, the hose compression must be adjusted during the life of the hose. During continuous use, the known wall thickness of the hose wears down to an unknown value. In such a situation, it is very difficult to establish valid rules to be applied in conventional techniques of correct adjustment of hose compression. Invalid adjustment rules must be complemented with practical operating experience that frequently invokes serious over-compression and pump damage situations. In contrast, the present adjustment mechanism allows runtime adjustment of hose compression to be carried out.

The present invention is not limited to the above-described embodiments, but may be varied according to the appended claims. The adjustment mechanism represents a substantial advancement in the construction of a peristaltic pump as to its efficiency, operational reliability and ease of service. The invention is characterized by adjustment mechanism in the form of gear unit and corresponding counterpart, which adjustment mechanism is configured to adjust the gap between the rotor outer surface and the pump cavity inner periphery. Such an adjustment mechanism can be easily arranged within pump cavity of different sizes (e.g. height of the pump can be from 500 mm upwards). Pumps having a height less than 500 mm, can also utilize the principles of the present solution, however an additional attention should be paid to the construction of elements.

The invention claimed is:

1. A peristaltic pump comprising:
at least an assembly comprising at least a rotor configured to compress a hose being positioned on a pump cavity inner perimeter and an adjustment mechanism configured to adjust the compression force imposed on the hose, said assembly being coupled to a crankshaft of a pump body, wherein the adjustment mechanism comprises at least a gear unit and a counterpart for said gear unit, said counterpart being operatively coupled to said rotor, wherein the gear unit comprises a shaft and at least one gear on each end of the shaft, wherein the counterpart comprises at least one counterpart piece on each end of the rotor, and wherein the gear unit in cooperation with the counterpart are configured to adjust a gap between an outer surface of the rotor and the pump cavity inner perimeter.

2. The peristaltic pump according to claim 1, further including supporting means configured to support said hose.

3. The peristaltic pump according to claim 1, wherein bearings of the crankshaft are arranged within the pump cavity.

4. The peristaltic pump according to claim 1, wherein the pump comprises a locking means configured to function in a locking position and a rest position, where the locking means in the locking position are configured to lock the adjustment mechanism, and wherein the locking means in the rest position are configured to enable the adjusting operation of the adjusting mechanism.

5. The peristaltic pump according to claim 1, wherein the gear unit is rotatable with a crank.

6. An apparatus for a peristaltic pump, said apparatus comprising:
a rotor configured to compress a hose being positioned on a pump cavity inner perimeter, and an adjustment mechanism configured to adjust the compression force imposed on the hose, said apparatus suitable for being coupled to a crankshaft of a pump body, wherein the adjustment mechanism comprises at least a gear unit and a counterpart for the gear unit, said counterpart being operatively coupled to said rotor, wherein the gear unit comprises a shaft and at least one gear on each end of the shaft, wherein the counterpart comprises at least one counterpart piece on each end of the rotor, and wherein the gear unit in cooperation with the counterpart are configured to adjust a gap between an outer surface of the rotor and the pump cavity inner perimeter.

7. The apparatus according to claim 6, wherein the apparatus comprises at least supporting means that are configured to support the hose.

8. The apparatus according to claim 6, wherein the apparatus comprises a locking means configured to function in a locking position and a rest position, where the locking means in the locking position are configured to lock the adjustment mechanism, and wherein the locking means in the rest position are configured to enable the adjusting operation of the adjusting mechanism.

9. The apparatus according to claim 6, wherein the gear unit is rotatable with a crank.

* * * * *